(12) United States Patent
Alshehri et al.

(10) Patent No.: US 10,718,702 B2
(45) Date of Patent: Jul. 21, 2020

(54) DYNAMIC CONTACT ANGLE MEASUREMENT

(71) Applicant: Saudi Arabian Oil Company, Dhahran (SA)

(72) Inventors: Amar Alshehri, Dhahran (SA); Abdulkareem AlSofi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 160 days.

(21) Appl. No.: 15/888,873

(22) Filed: Feb. 5, 2018

(65) Prior Publication Data
US 2019/0242804 A1 Aug. 8, 2019

(51) Int. Cl.
*G01N 13/02* (2006.01)
*G01N 33/24* (2006.01)
(Continued)

(52) U.S. Cl.
CPC ............ *G01N 13/02* (2013.01); *G01B 11/26* (2013.01); *G01N 1/28* (2013.01); *G01N 33/24* (2013.01);
(Continued)

(58) Field of Classification Search
CPC .......... G01B 11/26; G01N 13/02; G01N 1/28; G01N 2013/0208; G01N 2013/0241; G01N 33/24; G06T 7/60
See application file for complete search history.

(56) References Cited

U.S. PATENT DOCUMENTS

| 4,688,938 A | 8/1987 | Demoulin et al. |
| 5,861,946 A | 1/1999 | Hudson et al. |

(Continued)

FOREIGN PATENT DOCUMENTS

| JP | 4563890 | 10/2010 |
| JP | 2017037080 | 2/2017 |

(Continued)

OTHER PUBLICATIONS

Mahani, Hassan & Berg, Steffen & Ilic, Denis & Bartels, Willem-Bart & Niasar, Vahid. (2013). Kinetics of the Low Salinity Waterflooding Effect Studied in a Model System (SPE 165255). 10.2118/165255-MS. (Year: 2013).*

(Continued)

*Primary Examiner* — Violeta A Prieto
(74) *Attorney, Agent, or Firm* — Fish & Richardson P.C.

(57) ABSTRACT

A contact angle measurement system includes a housing that can hold a volume of a first fluid having a first density, an adjustable rock sample holder positioned within the housing, a fluid dropper attached to the housing, an image capturing device, and a computer system. The holder can support a rock sample. An orientation of the holder relative to the housing is adjustable such that an outer surface of the rock sample is at a non-zero angle relative to a lower wall of the housing. When the orientation of the holder relative to the housing is such that the outer surface of the rock sample is at the non-zero angle relative to the lower wall, the fluid droplet traverses the outer surface of the rock sample. The image capturing device can capture images of the fluid droplet as the fluid droplet traverses the outer surface of the rock sample.

14 Claims, 10 Drawing Sheets

(51) Int. Cl.
G01N 1/28 (2006.01)
G01B 11/26 (2006.01)
G06T 7/60 (2017.01)

(52) U.S. Cl.
CPC .............. G01N 2013/0208 (2013.01); G01N 2013/0241 (2013.01); G06T 7/60 (2013.01)

(56) References Cited

U.S. PATENT DOCUMENTS

| | | | |
|---|---|---|---|
| 6,982,787 B1 | 1/2006 | Wapner et al. | |
| 7,699,782 B2* | 4/2010 | Angelsen ................ | A61B 8/12 600/444 |
| 8,474,306 B1 | 7/2013 | Behroozi | |
| 8,768,628 B2 | 7/2014 | Ghedan et al. | |
| 9,016,111 B2 | 4/2015 | Stukan et al. | |
| 9,086,354 B2* | 7/2015 | AlSahan ............ | B01D 17/0214 |
| 9,675,994 B2 | 6/2017 | Schoenfisch | |
| 2005/0212869 A1 | 9/2005 | Ellson | |
| 2012/0181019 A1 | 7/2012 | Saini et al. | |
| 2013/0152668 A1 | 6/2013 | Stukan et al. | |
| 2014/0147627 A1 | 5/2014 | Aizenberg | |
| 2015/0086451 A1* | 3/2015 | Torem ..................... | C22B 26/20 423/157.3 |
| 2015/0211973 A1 | 7/2015 | Friedrich et al. | |
| 2015/0233223 A1 | 8/2015 | Alameri et al. | |
| 2015/0259754 A1 | 9/2015 | Kaler | |
| 2016/0272873 A1 | 9/2016 | Mahadevan et al. | |
| 2016/0339424 A1 | 11/2016 | Megaridis | |
| 2019/0094120 A1* | 3/2019 | Gmira .................... | G01N 33/24 |
| 2019/0242803 A1* | 8/2019 | AlGeer ................ | G01B 11/26 |

FOREIGN PATENT DOCUMENTS

| | | | |
|---|---|---|---|
| JP | 2017037080 A | * | 2/2017 |
| WO | 2012140338 | | 10/2012 |

OTHER PUBLICATIONS

International Search Report and Written Opinion issued in International Application No. PCT/US2019/015554 dated Apr. 9, 2019, 19 pages.
Rao "Measurements of dynamic contact angles in solid-liquid-liquid systems at elevated pressures and temperatures," Colloids and Surfaces A: Physiochemical and Engineering Aspects, vol. 206, No. 1-3, Jul. 1, 2002, 14 pages.
International Search Report and Written Opinion issued in International Application No. PCT/US2019/015758 dated Apr. 9, 2019, 16 pages.
Lamour et al., "Contact Angle measurements using a simplified experimental set-up," Journal of Chemical Education, vol. 87, No. 12, Dec. 2010, 5 pages.
Rao, "Correlation of Oil-Water Flow Behavior in Reservoir Rocks with Dynamic Contact Angles," Journal of Canadian Petroleum Technology, vol. 41, No. 7, Jul. 2002, 8 pages.
Shedid and Ghannam, "Factors affecting contact-angle measurement of reservoir rocks," Journal of Petroleum Science and Engineering, vol. 44, Nov. 2004, 12 pages.
Yousef et al., "The Impact of the Injection Water Chemistry on Oil Recovery from Carbonate Reservoirs," SPE-154077, presented at the SPE EOR Conference at Oil and Gas West Asia, Apr. 16-18, 2012, 14 pages.
Alshakhs, "An Experimental Study of the Impact of Injection Water Composition on Oil Recovery from Carbonate Rocks," A Dissertation Submitted to the Department of Energy Resources Engineering and the Committee on Graduate Studies of Stanford University in Partial Fulfillment of the Requirements for the Degree of Doctor of Philosophy, Jun. 2015, 171 pages.
Alshehri, "An X-Ray CT Study of Multidimensional Imbibition in Dual Porosity Carbonates," A Dissertation submitted to the Department of Energy Resources Engineering and the Committee on Graduate Studies of Stanford University in Partial Fulfillment of the Requirements for the Degree of Doctor of Philosophy, Oct. 2013, 434 pages.
Attension, "Static and dynamic contact angles and their measurement techniques," Biolin Scientific, available on or before Aug. 2017, 3 pages.
Dyne Testing, "Contact Angle Measurement Equipment," Dyne Testing Ltd, available on or before Dec. 26, 2016, 2 pages.
Extrand and Yumagai, "An experimental study of contact angle hysteresis," Journal of Colloid and Interface Science vol. 191, Apr. 18, 1997, 7 pages.
Extrand and Yumagai, "Contact angles and hysteresis on soft surfaces," Journal of Colloid and Interface Science vol. 184, Jul. 16, 1996, 11 pages.
Kruss, "Comparison of Wilhelmy and Sessile Drop Technique: A practical comparison of the techniques used to measure contact angles for liquids on non-porous solids," 1996 Annual Meeting of the Society of Tribologists and Lubrication Engineers, Lubrication Engineering, Tribology Transactions, Jan. 1996, 4 pages.
Kruss, "Drop Shape Analyzer—DSA100," Kruss: Advancing your Surface Science, available on or before Aug. 22, 2017, retrieved from URL <https://www.kruss-scientific.com/products/contact-angle/dsa100/drop-shape-analyzer-dsa100e/>, 8 pages.
Kruss, "Drop Shape Analyzer—DSA25," Kruss: Advancing your Surface Science, available on or before Aug. 22, 2017, retrieved from URL <https://www.kruss-scientific.com/products/contact-angle/dsa25/drop-shape-analyzer-dsa25/>, 4 pages.
Kruss, "Drop Shape Analyzer—DSA30," Kruss: Advancing your Surface Science, available on or before Jun. 2014, 4 pages.
Kruss-Scientific.com [online], "Advancing Angle," available on or before Aug. 21, 2017, retrieved from URL<https://www.kruss.de/services/education-theory/glossary/advancing-angle/>, 1 page.
MacDougall and Ockrent, "Surface energy relations in liquid/solid systems I. The adhesion of liquids to solids and a new method of determining the surface tension of liquids," Proceedings of the Royal Society of Medicine of London, vol. 180, Jun. 5, 1942, 23 pages.
Roberts et al., "Ultrasonic Removal of Organic Deposits and Polymer Induced Formation Damage," SPE Formation Damage Control Symposium, Feb. 14-15, 1996, 9 pages.
Vinci Technologies, "Interfacial Tension Measurements with IFT 700," Vinci Technologies, available on or before May 2010, 5 pages.
Yuan and Lee, "Contact angle and wetting properties," Springer Verlag Berlin Heidelberg, Springer Series in Surface Sciences vol. 51, 2013, 33 pages.
International Search Report and Written Opinion issued in International Application No. PCT/US2018/052434 dated Dec. 20, 2018, 13 pages.
Mahani et al., "Kinetics of the Low Salinity Waterflooding Effect Studied in a Model System," SPE Enhanced Oil Recovery Conference, Jul. 2, 2013, 14 pages.
Alshakhs et al., "Understanding the role of brine ionic composition on oil recovery by assessment of wettability from colloidal forces," Advances in Colloid and Interface Science, Elsevier, vol. 233, Aug. 20, 2015, 13 pages.

* cited by examiner

DYNAMIC CONTACT ANGLE MEASUREMENT

TECHNICAL FIELD

This specification relates to dynamic contact angle measurement for determining wettability of rock formations.

BACKGROUND

Wettability is a property to measure the interaction between a fluid and a solid surface in the presence of other immiscible fluids. Wettability can be defined by the contact angle of the fluid with the solid surface. Regarding oil production, the wettability of a rock formation can affect the oil extraction process. Rock formations can be described as being water-wet, intermediate wet, or oil-wet, which translate to contact angle ranges of approximately 0° to 75°, 75° to 105°, and 105° to 180°, respectively. A shift from oil-wetness to water-wetness of a rock formation can generally increase oil production from the formation.

Contact angle measurement can include observing the behavior of a small amount of fluid, such as a droplet or gas bubble, on a solid surface. Contact angle measurements can be taken on a stationary droplet (static contact angle) or a moving droplet (dynamic contact angle). Porous media, such as rock, is typically more complex and can have several configurations due to the varied geometry and mineralogy of pore space. The wettability of rock formations can therefore be heterogeneous, and heterogeneous wettability can further affect hydrocarbon recovery from rock formations in which the hydrocarbons are trapped.

SUMMARY

The present disclosure describes technologies relating to dynamic contact angle measurement.

Certain aspects of the subject matter described here can be implemented as a contact angle measurement system that includes a housing that can hold a volume of a first fluid having a first density, an adjustable rock sample holder positioned within the housing, a fluid dropper attached to the housing, an image capturing a device, and a computer system. The housing includes an upper wall, a lower wall below the upper wall, and side walls connecting the upper wall and the lower wall. The upper wall, the lower wall, and the side walls define an enclosure to hold the volume of the first fluid. The holder can support a rock sample, and an orientation of the holder relative to the housing is adjustable such that an outer surface of the rock sample is at a non-zero angle relative to the lower wall of the housing. The fluid dropper is positioned relative to the holder to add a fluid droplet of a second fluid, whose contact angle is to be measured, on a surface of the rock sample facing the lower wall when the rock sample is supported by the holder. The second fluid has a second density lighter than the first density of the first fluid. When the orientation of the holder relative to the housing is such that the outer surface of the rock sample is at the non-zero angle relative to the lower wall of the housing, the fluid droplet traverses the outer surface of the rock sample. The image capturing device can capture images of the fluid droplet as the fluid droplet traverses the outer surface of the rock sample. The computer system includes one or more processors and a computer-readable medium storing instructions executable by the one or more processors to perform operations. The operations include receiving digitized versions of the images of the fluid droplet dropped on the rock sample and determining, based on one or more of the images, a contact angle of the fluid droplet relative to a surface of the rock sample on which the fluid droplet is dropped.

This, and other aspects, can include one or more of the following features.

The holder can include a stationary plate on a first end of the holder, a moveable plate on a second end of the holder opposite the first end, and a plate-adjusting screw running through the upper wall of the housing and coupled to the moveable plate. The plate-adjusting screw can adjust a position of the moveable plate.

The upper wall, the lower wall, and the side walls can form an enclosure, and the holder can be attached to the upper wall.

The system can include multiple clips, each attached to the holder. The clips can be spaced apart from each other by a distance in which the holder is positioned.

The system can include an adjustable screw attached to one of the clips. The screw can change the distance between the clips.

The adjustable screw can be a first adjustable screw attached to a first clip, and the apparatus can include a second adjustable screw attached to a second clip. The first adjustable screw and the second adjustable screw can independently change the distance between the clips.

The first fluid can include water, and the second fluid can include hydrocarbon.

The system can include a heating circuit that can heat the first fluid. The heating circuit can be positioned within the housing.

The heating circuit can be embedded within the lower wall of the housing.

The heating circuit can include a fluid-carrying pipe embedded within the lower wall.

The upper wall of the housing can include an opening, and the fluid dropper can include a J-needle positioned within the opening in the upper wall of the housing.

The system can include a sonicator attached to the housing. The sonicator can generate a sound wave, and the housing can transmit the sound wave to the fluid droplet on the rock sample. The sound wave can sonically remove the fluid droplet from the rock sample.

The sonicator can include a transducer that can generate the sound wave in response to receiving power from a power source. An outer surface of a wall of the housing can include a groove, and the transducer can be embedded in the groove.

The sonicator can remove the fluid droplet from the rock sample without removing the rock sample or the holder from the housing.

Certain aspects of the subject matter described here can be implemented as a method. A rock sample is at least partially submerged in a first fluid having a first density. The rock sample is supported by a rock sample holder positioned within a housing. A fluid droplet of a second fluid is added on a surface of the rock sample. The second fluid has a second density lighter than the first density of the first fluid. While retaining the rock sample on the holder, the rock sample holder is adjusted to be offset from a horizontal, thereby causing the fluid droplet to traverse the surface of the rock sample. While the fluid droplet traverses the surface of the rock sample, a contact angle measurement is performed on the fluid droplet with reference to the surface of the rock sample.

This, and other aspects, can include one or more of the following features.

The holder can include a stationary plate on a first end of the holder, a moveable plate on a second end of the holder opposite the first end, and a plate-adjusting screw running through a wall of the housing and coupled to the moveable plate.

Adjusting the rock sample holder can include adjusting a position of the moveable plate using the plate-adjusting screw.

After performing the contact angle measurement and while retaining the rock sample on the holder, the first fluid can be sonicated within the housing to cause the fluid droplet to be removed from the outer surface of the rock sample.

The first fluid can include water. The medium can be sonicated without removing the holder from the housing by positioning an ultrasonic transducer in a groove formed on an outer surface of a wall of the housing and supplying power to the ultrasonic transducer. The ultrasonic transducer can generate an ultrasonic sound wave that sonicates the fluid droplet in response to the supplied power.

The details of one or more implementations of the subject matter of this specification are set forth in the accompanying drawings and the description. Other features, aspects, and advantages of the subject matter will become apparent from the description, the drawings, and the claims.

DETAILED DESCRIPTION

Figure 1:
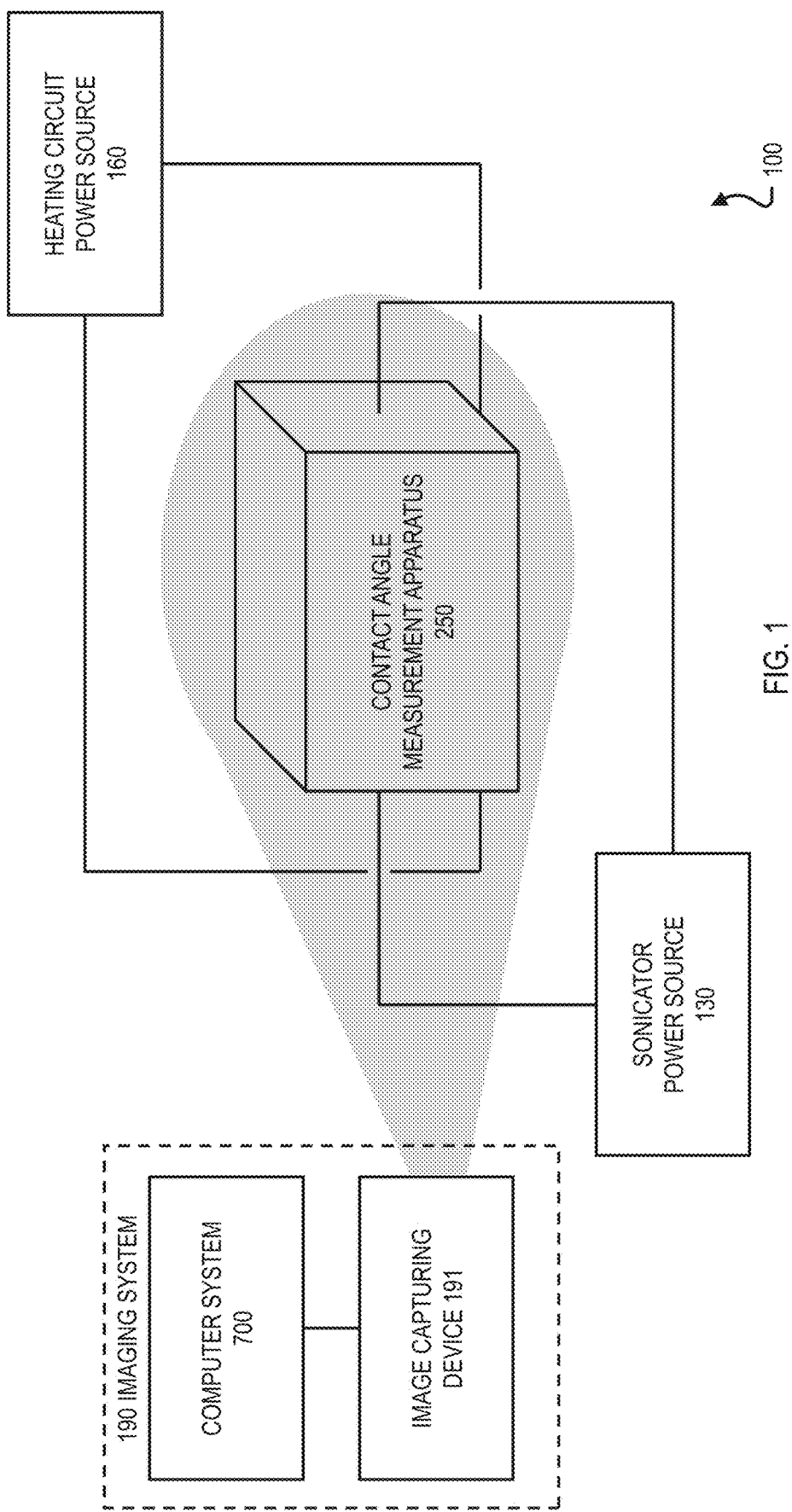
FIG. 1 is a schematic diagram of an example of a contact angle measurement system.

Surface tension, interfacial tension, and contact angle relate to wettability. Surface tension is a measure of how much force it takes to keep a liquid together. Interfacial tension is a measure of adhesive force between one fluid and the gas, liquid, or solid phase of another substance. A surface is considered to have a high wettability in relation to a fluid if its attractive force to the fluid (interfacial tension) is stronger than the fluid's surface tension, which causes the fluid to spread out over the surface and results in a low contact angle. Surface tension and contact angle can be measured utilizing optical techniques and drop shape analysis.

Surface tension of a fluid can be measured utilizing different methods, for example, the pendant drop method. The pendant drop method includes suspending a drop of fluid from a needle in a bulk liquid or gas phase. The shape of the drop can depend on the relationship between the surface tension or interfacial tension and gravity. A light source can direct light on and through the droplet, and the resulting shadow image of a pendant drop can be recorded and analyzed to determine pendant drop curvature and deformation effect due to gravity. The degree of deviation from a spherical shape can be provided by a ratio between weight of the droplet and its surface tension. In the case that the density difference between the phases is known, the surface tension can be calculated from the shape of the drop. With respect to oil and gas applications, the bulk liquid phase can be water or brine, and the droplet can be oil, which is lighter than water or brine. For oil in water applications, the oil droplet is inverted, as the oil tends to rise in comparison to the heavier surrounding fluid. The interfacial tension can be determined utilizing the pendant drop method and can be used to help determine the suitability of water or brine for injection into a rock formation in enhanced oil recovery.

Another method to measure the contact angle of a fluid on a surface is the sessile drop method. The sessile drop method includes depositing a drop of fluid onto a surface. The contact angle is the angle between the droplet and the surface. A light source can direct light on and through the droplet, and the resulting shadow image of a droplet on a surface can be recorded and analyzed to determine the contact angle. The droplet shape on the surface can be modelled as a drop shape function. Examples of drop shape functions utilized in modelling include circular, for contact angles approximately in a range of 0 degrees (°) to 20°; conic section, for contact angles approximately in a range of 10° to 100°; polynomial, for contact angles approximately in a range of 10° to 180°; and Young-Laplace, for contact angles approximately in a range of 10° to 180°. For oil in water applications, the oil droplet is released under a solid surface, so that it rises through the bulk liquid (water or brine) and rests on the solid surface. The measured contact angle can characterize the sample (and therefore, rock formation) as oil-wet, intermediate wet, or water-wet in relation to the chosen bulk fluid (water or brine). If the sample wettability shifts toward water-wet in a brine, the brine can be a suitable candidate for injection into the rock formation to increase oil extraction.

With existing contact angle measurement apparatuses, in order to run another measurement test after one is complete, the setup may require dismantling, cleaning, re-filling, and use of a new rock sample. In cases that the apparatus operates at a high temperature, such as 90 degrees Celsius (° C.), the apparatus may need some time to cool down before it is dismantled. This specification describes an apparatus that can utilize sonication to detach an oil droplet from a rock sample without dismantling the apparatus and without damaging the rock sample, so that a new oil droplet can be added to the same rock sample and another contact angle measurement test can be performed.

Particular implementations of the subject matter described in this specification can be implemented so as to realize one or more of the following advantages. The benchtop contact angle measurement system is compact. The adjustable chip holder provides flexibility in size of a rock sample that can be tested in the system. Sonication capability allows for multiple, repeated contact angle measurements to be performed on a rock sample. In particular, a droplet can be removed from the surface of the rock sample without requiring that the sample be removed from the system or from the holder on which the sample rests. Instead, the droplet can be removed through sonication while the sample remains on the holder.

As shown in FIG. 1, a contact angle measurement system 100 can include a bench-top contact angle measurement apparatus 250, a sonicator power source 130, a heating circuit power source 160, and an imaging system 190. The apparatus 250 can include a housing 200 (refer to FIGS. 2A, 2B, 2C, and 2D). The housing 200 can include an upper wall 290A, a lower wall 290B below the upper wall 290A, and side walls 290C that connect the upper wall 290A and the lower wall 290B to form an enclosure 295. The housing 200 can include a holder 203 that is attached to the upper wall 290A and positioned within the enclosure 295 to hold a rock sample 201 or chip immersed in a bulk fluid, such as water or brine. The walls (290A, 290B, 290C) of the housing 200 can be made of a material that is transparent to light, such as acrylic glass, butyrate (for example, cellulose acetate butyrate), polycarbonate, and glycol-modified polyethylene terephthalate (PETG). The side walls 290C are conductive to sound.

The housing 200 can include a heating circuit 170 that can maintain a temperature of the bulk fluid that emulates subterranean conditions of a rock formation, for example, 90° C. The temperature of the bulk fluid is cooler than the boiling point of the bulk fluid. For example, the temperature of the bulk fluid can be at least 10° C. cooler than the boiling point of the bulk fluid. The heating circuit 170 can circulate a heating fluid, such as water, through an outer portion of the housing 200, utilizing a pump 173. The heating circuit 170 can heat the heating fluid to and maintain the heating fluid at a temperature using a heater 175, and temperature controller 177 that can be connected to the heating circuit power source 160.

The apparatus 250 can include a sonicator 131 that is connected to the sonicator power source 130 and can apply sound energy to agitate the bulk fluid. The sonicator 131 can be a device made of piezoelectric material, which can mechanically deform in response to an electric impulse. Periodic variation of amplitude, frequency, or both of the electric impulse can cause the piezoelectric device to deform and produce a sound wave. The electric impulse applied to the sonicator 131 can cause the transducer 135 to vibrate at ultrasonic frequencies, for example, greater than 20 kilohertz (kHz).

Referring back to FIG. 1, the imaging system 190 can include an image capturing device 191 and a computer system 700 coupled to the image capturing device 191. The image capturing device 191 is configured to capture an image of a fluid droplet dropped on the rock sample 201. The image capturing device 191 can include a camera and a light source. The light source can shine light on the apparatus 250, and the camera can capture image data which can be processed by the computer system 700 to calculate and determine a contact angle between a droplet of fluid, such as an oil droplet, and a surface of the rock sample 201. The computer system 700 can include one or more processors and a computer-readable medium that stores instructions executable by the one or more processors. The instructions, when executed by the one or more processors, can cause the one or more processors to perform operations. The operations can include receiving a digitized version of the image of the fluid droplet dropped on the rock sample 201. The operations can include determining, based on the image, a contact angle of the fluid droplet relative to a surface of the rock sample 201 on which the fluid droplet is dropped. The contact angle measurement system 100 can be compact in size and suitable to perform contact angle measurements on top of a laboratory bench. The sonicator 131 allows multiple measurement test runs to be performed on the rock sample 201.

Figure 2A:
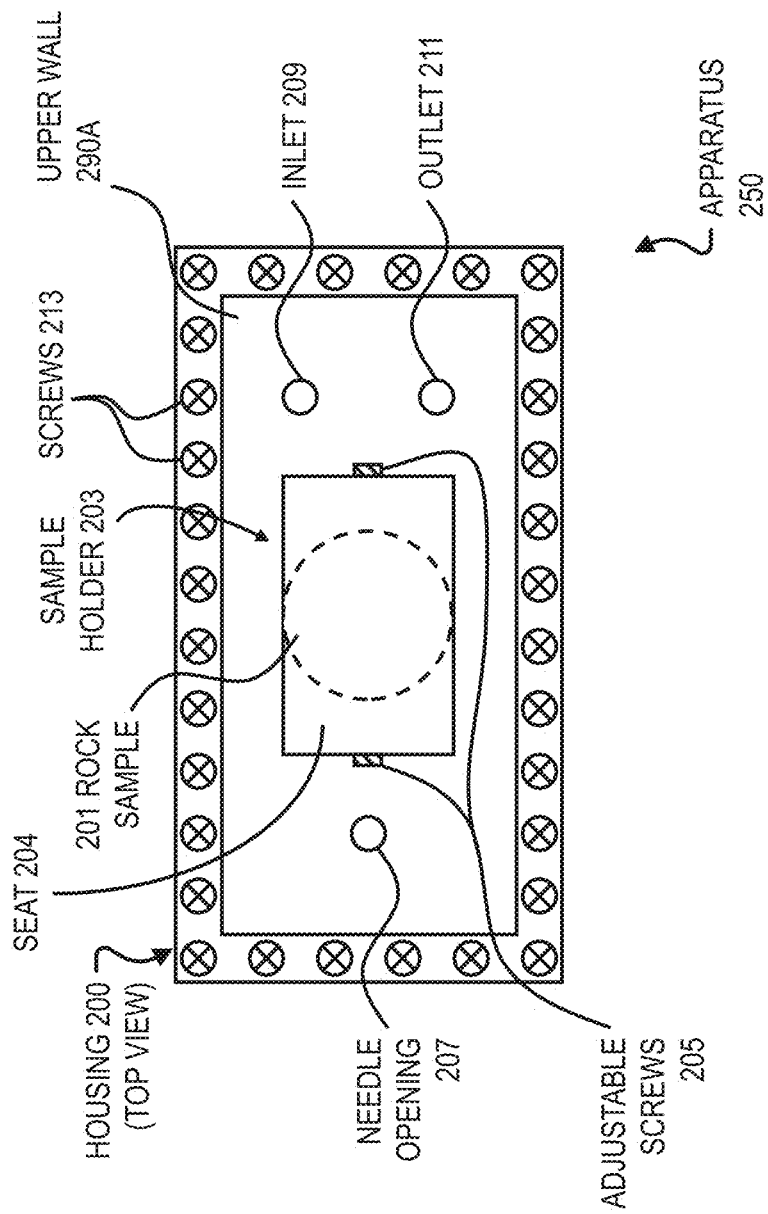
FIG. 2A is a top view of an example of a contact angle measurement system.

FIG. 2A illustrates a top view of an exemplary bench-top measurement housing 200. In certain implementations the upper wall 290A of the housing 200 can be fastened to the side walls 290C of the housing 200 by clips or screws 213. The holder 203 can be attached to the upper wall 290A of the housing 200. The holder 203 can hold a rock sample 201 that can have a cylindrical shape, for example, with a radius of approximately 10 to 15 millimeters (mm). The holder 203 can include one or more clips, each attached to the holder 203 and spaced apart from each other. Each clip can include a respective adjustable screw 205 that can be adjusted to change the distance between the clips and to accommodate various rock sample sizes. For example, the holder 203 can include two clips, each with an adjustable screw 205, where each adjustable screw 205 can independently change the distance between the two clips. The holder 203 can include a seat 204, where the rock sample 201 can be positioned in the seat 204. The seat 204 can prevent the rock sample 201 from falling off the holder 203 when a sound wave is transmitted to the fluid droplet on the rock sample 201.

The upper wall 290A of the housing 200 can include an inlet opening 209 and an outlet opening 211 to allow fluid to enter and exit the enclosure 295 of the housing 200. The enclosure 295 can be at least partially filled with a bulk fluid such as water or brine. The upper wall 290A of the housing 200 can include an opening, also referred to as a needle opening 207, that allows a fluid dropper 220 (shown in FIG. 2B) to be positioned within the opening 207 in the upper wall 290A of the housing 200.

Figure 2B:
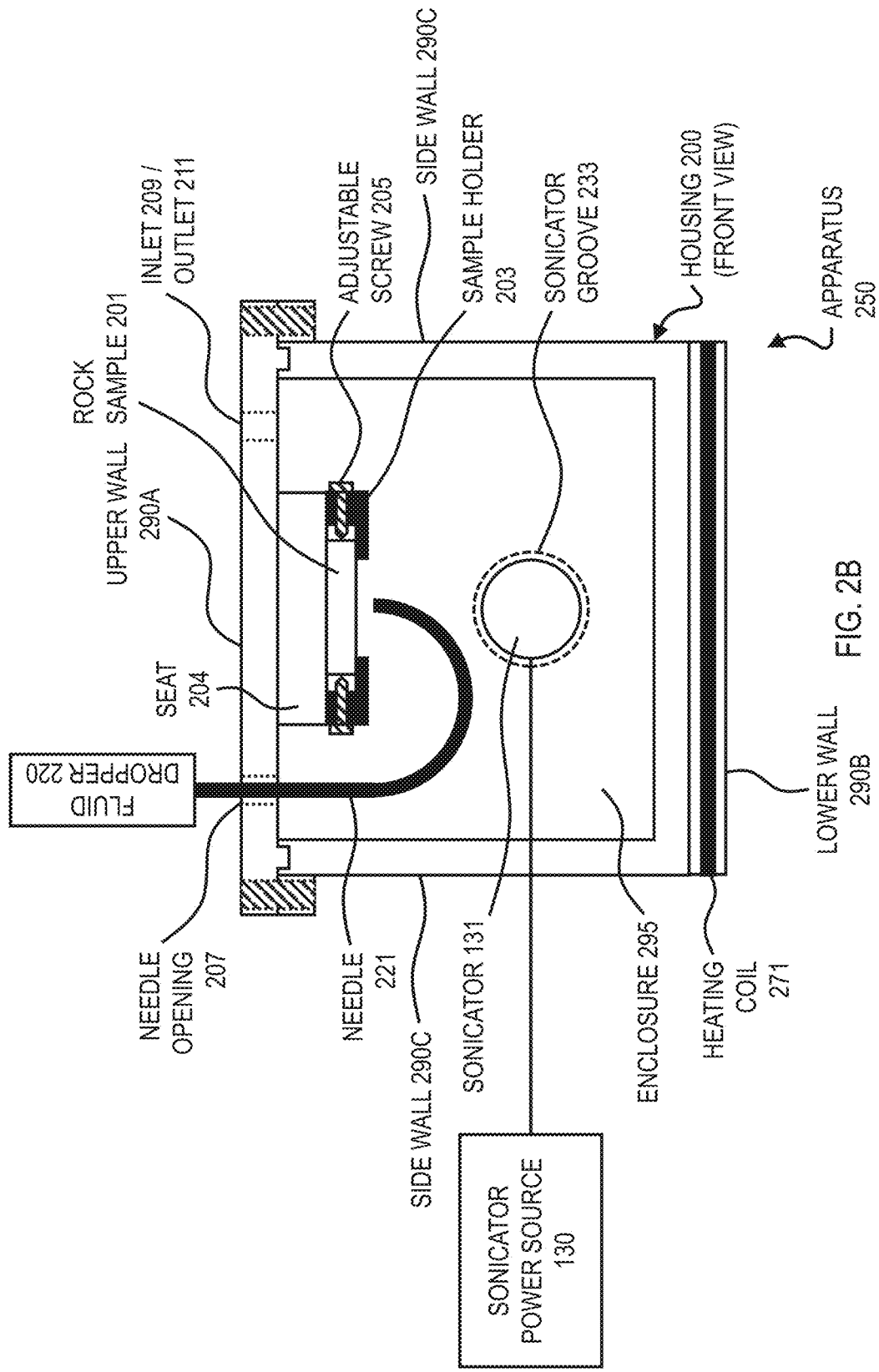
FIG. 2B is a front view of an example of the contact angle measurement system of FIG. 2A.
Figure 2C:
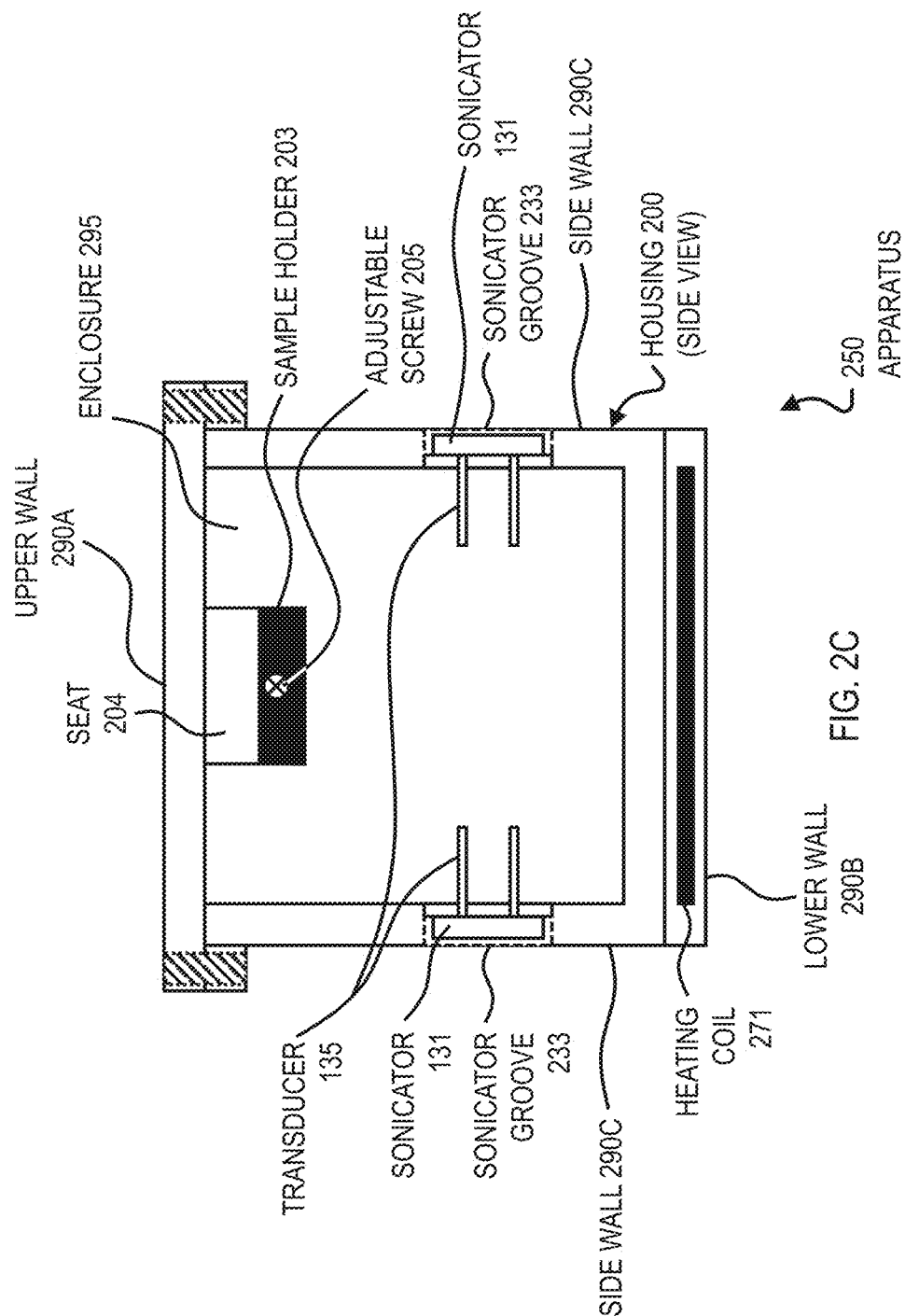
FIG. 2C is a side view of an example of the contact angle measurement system of FIG. 2A.

FIGS. 2B and 2C illustrate front and side views of an exemplary bench-top measurement housing 200, respectively. The apparatus 250 can include a heating coil 271 (described in more detail later) to maintain a desired temperature of the bulk fluid within the enclosure 295. The fluid dropper 220 can include a needle 221 and can be positioned through the needle opening 207 of the upper wall 290A of the housing 200, such that fluid can be injected into the enclosure 295 of the housing 200. The needle 221 can be configured to release fluid towards the upper wall 290A. For example, the needle 221 can have the shape of the letter J (also referred to as a J-needle), such that the needle outlet points in the general upward direction toward the bottom surface of the upper wall 290A of the housing 200. In the case that the bulk fluid is water or brine and the fluid injected by the needle 221 is oil, the oil has a lower density than the bulk fluid. Once a droplet is released by the needle 221, the droplet can rise (due to buoyancy) through the bulk fluid and contact and settle on the surface of the rock sample 201.

The housing 200 can include a sonicator groove 233 on the outer surface of a wall (290A, 290B, or 290C) of the housing 200. For example, the sonicator groove 233 can be located on the outer surface of the side wall 290C. The groove 233 can have any shape that allows the sonicator 131 to fit inside the groove 233 and be connected to the housing. The housing 200 can include as many grooves 233 as needed for the sonicator 131. For example, the housing 200 can include two sonicator grooves 233 on opposing walls. In certain implementations, the housing 200 can include one or more sonicator grooves 233 on the same wall, for example, the side wall 290C.

The sonicator 131 can have a cylindrical or cuboidal shape and can be compact in size. For example, the sonicator 131 can be cylindrical and have a diameter of approximately 10 mm and a total length of approximately 17 mm. The sonicator 131 can include a transducer 135 made of piezoelectric material that can deform and generate a sound wave in response to an electric impulse from a power source, such as the power source 130. For example, the sonicator 131 can include two transducers 135 in the form of two piezoelectric prongs that extend from the cylindrical portion of the sonicator 131 and into the enclosure 295, such that the transducers 135 are in contact with the bulk fluid. The sonicator 131 can be tunable, that is, the power supplied to the sonicator 131 can be adjusted to vary the frequency of the sound wave generated by the sonicator 131. The bulk fluid, such as water or brine, can transmit the sound wave generated by the sonicator 131 to a fluid droplet, such as an oil droplet, on a surface of the rock sample 201. The sound wave generated by the sonicator 131 can cause the droplet of fluid on the rock sample 201 to break apart into smaller droplets. The sound wave generated by the sonicator 131 can cause the droplet (or multiple droplets) of fluid on the surface of the rock sample 201 to travel across and off the surface of the rock sample 201. If the level of bulk fluid in the enclosure 295 is a level at which the sample 201 is submerged, once the fluid droplet travels off the surface of the rock sample 201, the fluid droplet can float to the top of the level of bulk fluid in the enclosure 295. The seat 204 of the holder 203 can prevent the rock sample 201 from falling off the holder 203 when the sound wave is transmitted to the fluid droplet. The sonicator 131 can agitate the bulk fluid, and the bulk fluid can transfer the sound wave from the sonicator 131 to the fluid droplet. The sonication can cause any droplets deposited onto the rock sample 201 to be removed from the rock sample 201 without removing the rock sample 201 or the holder 203 from the housing 200.

Figure 2D:
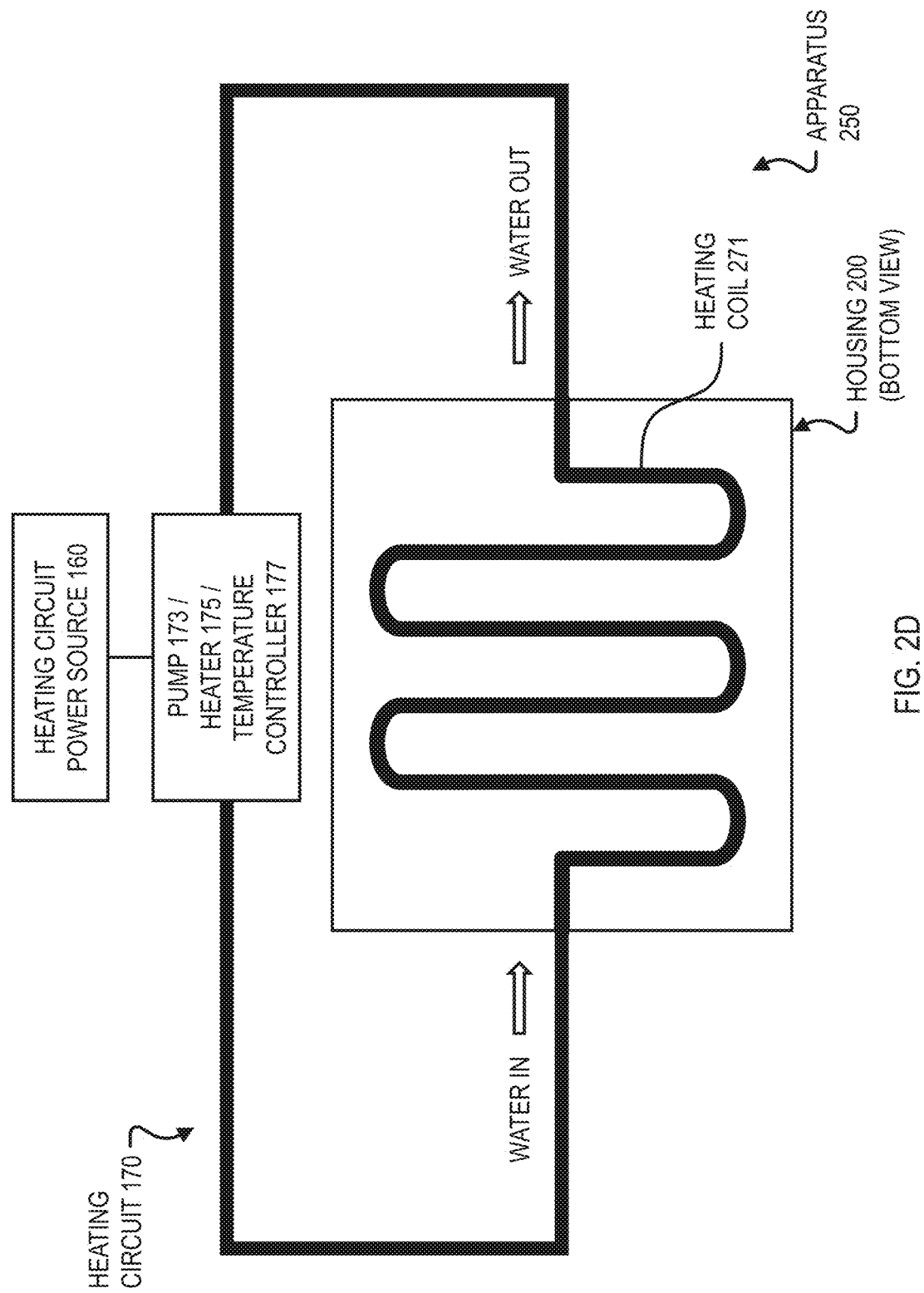
FIG. 2D is a bottom view of an example of the contact angle measurement system of FIG. 2A.

FIG. 2D illustrates a bottom view of an exemplary benchtop measurement housing 200. The heating circuit 170 described earlier can be embedded within the lower wall 290B of the housing 200. The heating circuit 170 can include a fluid carrying pipe, also referred to as a heating coil 271, that can be embedded within the lower wall 290B of the housing 200. The heating coil 271 can be made of steel or other heat-conductive material, and can optionally span multiple walls, for example, two side walls 290C of the housing 200. In certain implementations, the heating coil 271 can penetrate the walls (290A, 290B, 290C) of the housing 200, such that the heating coil 271 is in direct contact with the bulk fluid within the enclosure 295 of the housing 200. A heating fluid, such as water or other heat-conductive fluid, can pass through the heating coil 271 to provide heating to the apparatus 250, so that a bulk fluid temperature can be maintained. The pump 173 can circulate the heating fluid, and the temperature controller 177 can control the heater 175 to re-heat the heating fluid after it has passed through the heating coil 271. In certain implementations, the apparatus 250 can include a thermometer (not shown) that measures the temperature of the bulk fluid in the enclosure 295 of the housing 200, and the temperature controller 177 can control the heater 175 in response to a temperature reading from the thermometer.

Figure 3:
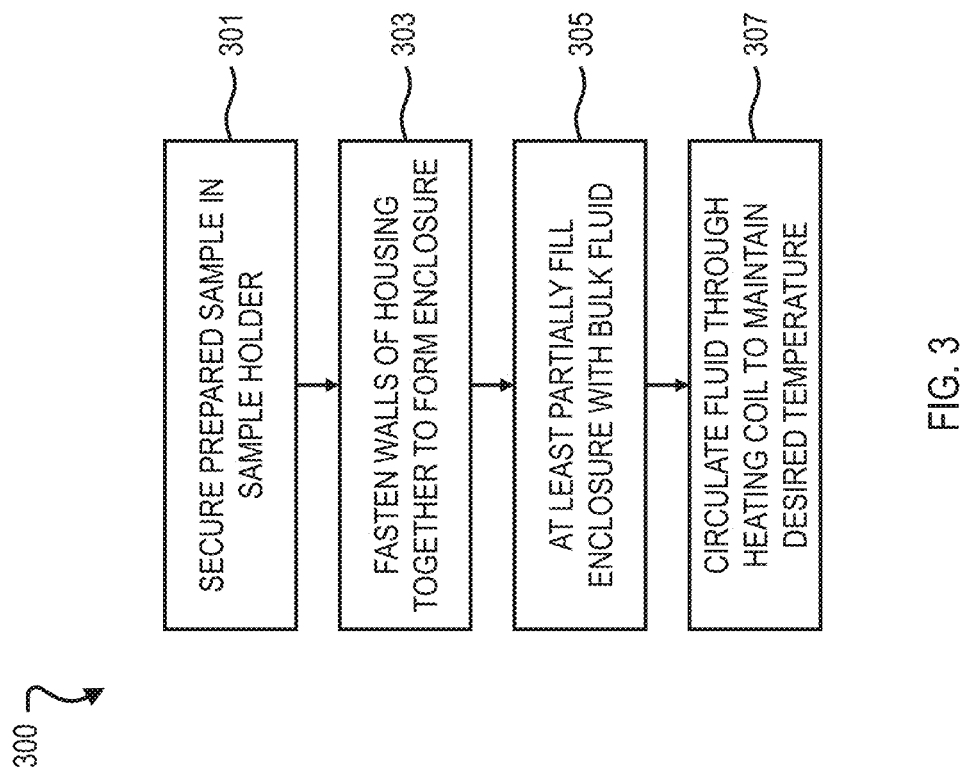
FIG. 3 is a flow chart illustrating an example method for assembling a contact angle measurement system.

FIG. 3 is a flow chart illustrating an example method 300 for assembling the contact angle measurement apparatus. At 301, a prepared rock sample 201 is secured in the sample holder 203, for example, using clips and the adjustable screws 205. The prepared rock sample 201 can be a chip that is cut from a rock, cleaned, polished, and aged in oil. At 303, the walls (290A, 290B, 290C) of the housing 200 are fastened together to form an enclosure 295. The walls (290A, 290B, 290C) of the housing 200 can be fastened together, for example, with screws 213. In some implementations, the side walls 290C are already connected to the lower wall 290B, so the upper wall 290A can be fastened to the side walls 290C to form the enclosure 295. In some implementations, all walls (290A, 290B, 290C) of the housing 200 are not connected to one other, so all of the walls (290A, 290B, 290C) can be fastened together to form the enclosure 295. The sample holder 203 can already be attached to the upper wall 290A, and the walls (290A, 290B, 290C) of the housing 200 can be fastened together in a way such that the sample 201 is positioned within the enclosure 295. At 305, the enclosure 295 is at least partially or completely filled with bulk fluid, such as water or brine. The level of bulk fluid in the enclosure 295 can be a level at which the sample 201 or the holder 203 is submerged. The bulk fluid can enter the housing 200 through the inlet opening 209. The bulk fluid can be pumped into the housing 200, for example, with a syringe or a pump. Bulk fluid or any unwanted fluid, such as air, can be pumped out of the enclosure 295 through the outlet opening 211. At 307, a heating fluid, such as water, is circulated through the heating coil 271 to maintain a desired temperature of the bulk fluid in the housing 200. The heating fluid can be circulated through the heating coil 271 at approximately 5° C. warmer than the desired temperature of the bulk fluid in the housing 200. For example, the heating fluid is circulated through the heating coil 271 at 95° C. to maintain a bulk fluid temperature of 90° C. in the housing 200. The heating fluid can operate at a sufficient pressure to avoid boiling of the heating fluid in the heating circuit 170. For example, the boiling point of water at 5 pounds per square inch gauge (psig) is approximately 115° C. Therefore, for a desired temperature of 90° C. in the bulk fluid within the housing 200, water can be supplied at approximately 10 psig and 95° C. in order to avoid boiling in the heating circuit 170.

Figure 4:
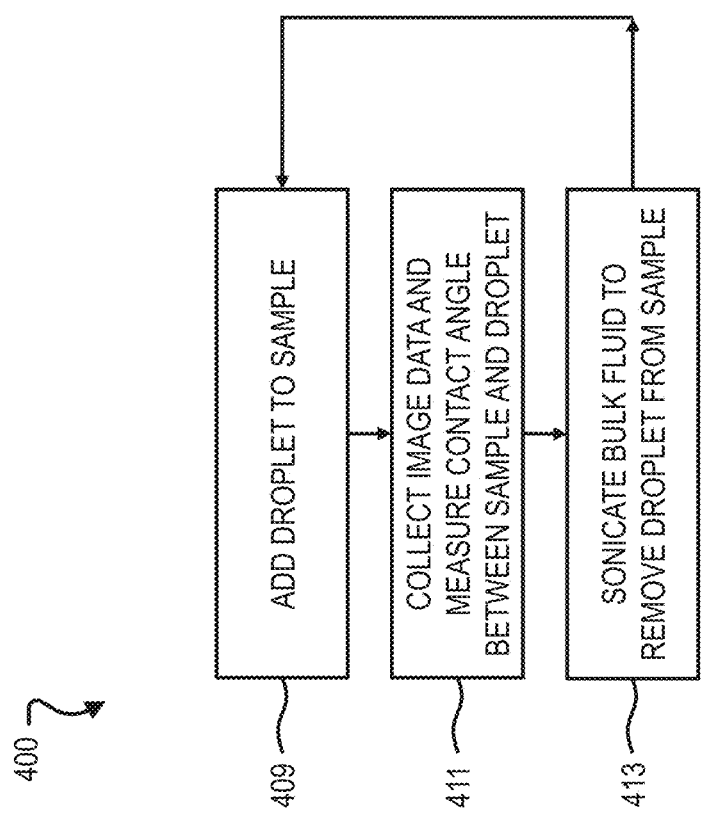
FIG. 4 is a flow chart illustrating an example method for measuring a contact angle.

FIG. 4 is a flow chart illustrating an example method 400 for conducting the contact angle measurement test. In some implementations, the test can be conducted using the contact angle measurement apparatus such as the one described earlier with reference to FIG. 3. At 409, a fluid droplet is added on an outer surface of the rock sample 201 supported by the rock sample holder 203 positioned within the housing 200. The fluid droplet, for example, an oil droplet, can be added on the outer surface of the rock sample 201 using a needle 221, such as a J-needle, positioned within the needle opening 207 in the upper wall 290A of the housing 200. At 411, a contact angle measurement is performed on the fluid droplet with reference to the outer surface of the rock sample 201. Contact angle measurement can include capturing an image of the fluid droplet on the outer surface of the rock sample and determining a contact angle of the fluid droplet on the outer surface, based on a digitized version of the captured image. For example, a shadow image of the fluid droplet and the rock sample can be obtained using a camera, a light source, and image processing by a computer system to determine contact angle.

At 413, while retaining the rock sample 201 on the holder 203, the medium (that is, bulk fluid) within the housing 200 can be agitated by the sonicator 131. The sonicator power source 130 can provide alternating current (AC) power to the transducer 135 in order to cause the transducer, which is composed of piezoelectric material, to vibrate. The power source 130 can supply voltage in the form of a sine wave or a square wave, for example, with a positive peak of 10 volts (V) and a negative peak of −10V. The sonication can cause the fluid droplet to be removed from the outer surface of the rock sample 201 as described earlier with reference to FIGS.

2B and 2C. The medium (or bulk fluid) can include water or brine and can transfer a sound wave from the sonicator 131 to the fluid droplet. Sonicating the medium can be performed without removing the holder 203 from the housing 200. An ultrasonic transducer (sonicator 131) can be positioned in a groove 233 formed on the outer surface of a wall (290A, 290B, 290C) of the housing 200. Power can be supplied to the ultrasonic transducer, in response to which the ultrasonic transducer (sonicator 131) can generate an ultrasonic sound wave that can sonicate the fluid droplet. Sonication can continue until the fluid droplet detaches and moves off the rock sample 201.

If desired, another contact angle measurement can be performed on the same rock sample 201. After removing the first fluid droplet from the outer surface of the rock sample 201 in response to sonicating the medium (or bulk fluid) at 413, the method 400 can be repeated. Therefore, the method 400 can include performing multiple contact angle measurements on multiple fluid droplets added on the outer surface of the rock sample 201 supported by the rock sample holder 203 positioned within the housing 200, where each contact angle measurement is performed one measurement at a time. After performing a contact angle measurement on a first fluid droplet and before performing a subsequent contact angle measurement on a second fluid droplet, the medium (or bulk fluid) can be sonicated within the housing 200 to remove the first droplet. Sonicating the medium (or bulk fluid) can be performed while retaining the rock sample 201 on the holder 203. An ultrasonic transducer (sonicator 131) can be positioned in a groove 233 formed on the outer surface of a wall (290A, 290B, 290C) of the housing 200. Power can be supplied to the ultrasonic transducer (sonicator 131), in response to which the ultrasonic transducer can generate an ultrasonic sound wave that can sonicate each fluid droplet.

Static contact angles can be used to assess static and quasi-static processes, and dynamic contact angles can be used to assess dynamic processes. A dynamic contact angle is the contact angle which occurs in the course of wetting or de-wetting of a solid. In the case of dynamic contact angle measurement, the measurement can be performed just before a fluid droplet begins to traverse a solid surface (that is, incipient movement) or while the fluid droplet is traversing the solid surface. The contact angle between the fluid droplet and the solid surface at the front of the droplet (that is, at the front of the direction of fluid droplet movement or incipient movement) is considered the advancing contact angle, while the contact angle between the fluid droplet and the solid surface at the back of the droplet (that is, the side of the fluid droplet that is trailing in the direction of fluid droplet movement or incipient movement) is considered the receding contact angle. In relation to core flooding methods, for example, the advancing contact angle can be used for imbibition steps (such as displacement of a non-wetting phase with a wetting phase), and the receding contact angle can be used for drainage steps (such as displacement of a wetting phase with a non-wetting phase).

Figure 5:
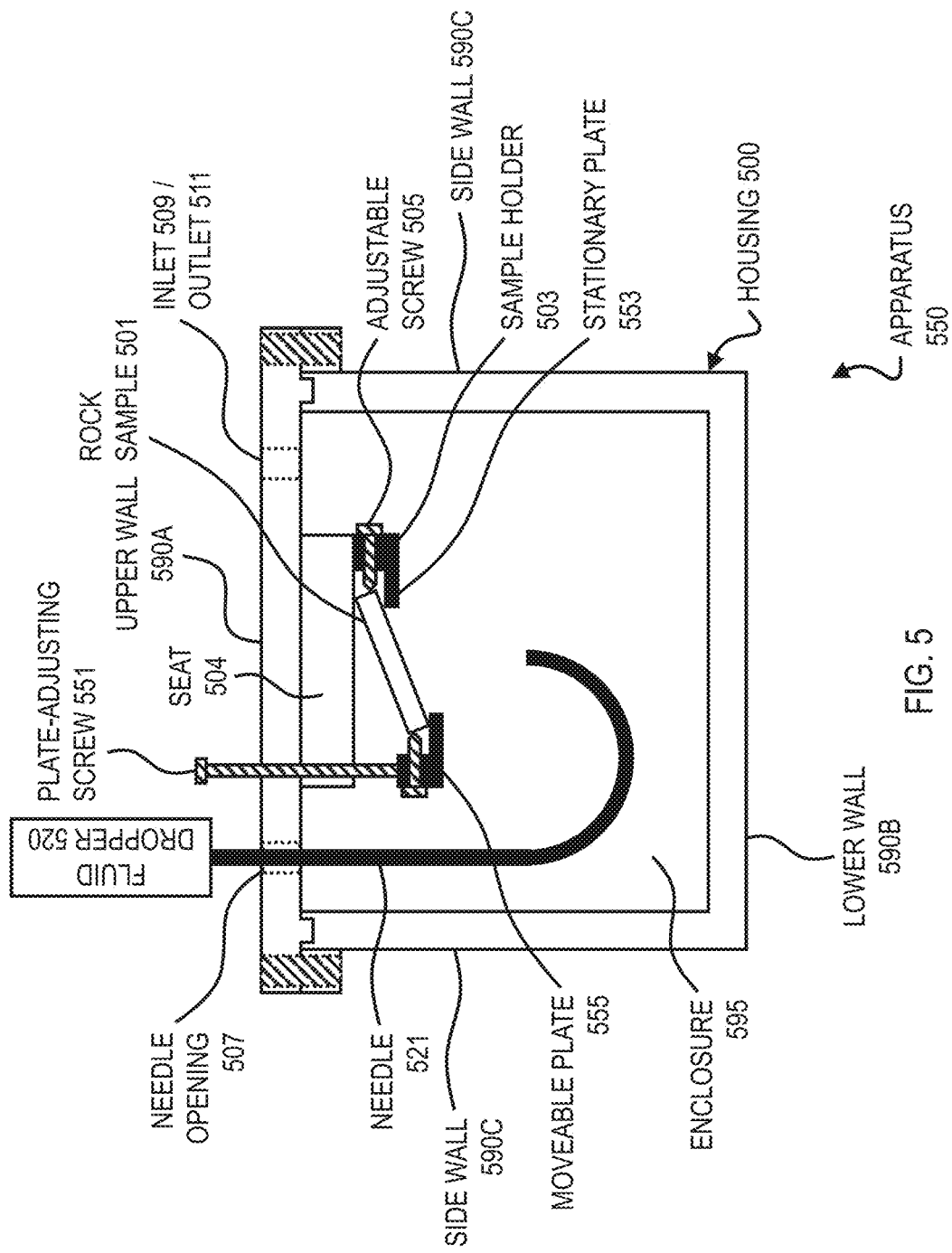
FIG. 5 is a front view of an example of a contact angle measurement system.

FIG. 5 shows an example of a contact angle measurement apparatus 550. The contact angle measurement apparatus 550 can include any or all of the components of the contact angle measurement apparatus 250 shown in FIGS. 2A, 2B, 2C, and 2D. For example, although not shown in FIG. 5, the contact angle measurement apparatus 550 can include a sonicator to remove fluid droplets from a rock sample and a heating circuit to maintain an operating temperature of a bulk fluid within the apparatus 550 similar to those described for the apparatus 250. The contact angle measurement apparatus 550 can be part of a contact angle measurement system (such as the system 100, in which the contact angle measurement apparatus 550 can replace the apparatus 250). The contact angle measurement apparatus 550 includes a housing 500 that can hold a volume of a first fluid having a first density. In some cases, the first fluid includes water. The housing 500 includes an upper wall 590A, a lower wall 590B below the upper wall 590A, and side walls 590C connecting the upper wall 590A and the lower wall 590B. The walls (590A, 590B, 590C) can form an enclosure 595. The contact angle measurement apparatus 550 includes an adjustable rock sample holder 503 positioned within the housing 500 (similar to the rock sample holder 203 of apparatus 250).

The rock sample holder 503 can support a rock sample 501, and an orientation of the sample holder 503 relative to the housing 500 is adjustable, such that an outer surface of the rock sample 501 is at a non-zero angle relative to the lower wall 590B of the housing 500. The rock sample holder 503 can be attached to the upper wall 590A and can include a stationary plate 553, a moveable plate 555, and a plate-adjusting screw 551. The stationary plate 553 can be positioned on a first end of the holder 503, the moveable plate 555 can be positioned on a second end of the holder 503 opposite the first end, and the plate-adjusting screw 551 can run through the upper wall 590A of the housing 500 and coupled to the moveable plate 555. The plate-adjusting screw 551 can be used to adjust a position of the moveable plate 555. The apparatus 550 includes a fluid dropper 520 (as another example, the fluid dropper 220) attached to the housing 500 and positioned relative to the holder 503 to add a fluid droplet of a second fluid (whose contact angle is to be measured) on a surface of the rock sample 501 facing the lower wall 590B when the rock sample 501 is supported by the holder 503. The second fluid can have a second density that is lighter than the first density of the first fluid. For example, the first fluid can be a water-based fluid, and the second fluid can be a lighter, hydrocarbon-based fluid, such as oil. The fluid dropper 550 can release a fluid droplet of the second fluid (hydrocarbon oil) from below the rock sample 501, and due to the density difference between the first fluid and the second fluid, the fluid droplet of the second fluid will rise through the first fluid and be added onto the surface of the rock sample 501 that is facing the lower wall 590B of the apparatus 550.

The plate-adjusting screw 551 can be used to move the moveable plate 555 upward and downward relative to the housing 500. For example, as a base position, the moveable plate 555 and the stationary plate 553 can be parallel to a horizontal (that is, the stationary plate 553 and the moveable plate 555 can be at the same height with respect to the lower wall 590B of the housing 500). The plate-adjusting screw 551 can be adjusted, such that the moveable plate 555 moves downward (that is, closer to the lower wall 590B of the housing 500). The rock sample 501, which is seated on and supported by the stationary plate 553 and the moveable plate 555, will tilt based on the offsetting of the moveable plate 555 from the horizontal. When the orientation of the holder 503 relative to the housing 500 is such that the outer surface of the rock sample 501 is at the non-zero angle relative to the lower wall 590B of the housing 500, the fluid droplet traverses the outer surface of the rock sample 501. In some implementations, the moveable plate 555 includes a ball joint that is coupled to a clip (such as the clips described for the holder 203) which secures the rock sample 501 in the rock sample holder 503. The ball joint can allow for free rotation of the clip and can allow the rock sample 501 to tilt smoothly whenever the moveable plate 555 is adjusted by the plate-adjusting screw 551.

As mentioned previously, the contact angle measurement apparatus 550 can be part of a contact angle measurement system like the contact angle measurement system 100. The system including the apparatus 550 can include an image capturing device (such as the device 191) that can capture multiple images of the fluid droplet as the fluid droplet traverses the outer surface of the rock sample. The system can also include a computer system (such as the computer system 700), which includes one or more processors and a computer-readable medium that stores instructions executable by the one or more processors. The instructions, when executed by the one or more processors, can cause the one or more processors to perform operations. The operations can include receiving digitized versions of the multiple images of the fluid droplet dropped on the rock sample. The operations can include determining, based on one or more of the multiple images, a contact angle of the fluid droplet relative to a surface of the rock sample on which the fluid droplet is dropped.

Figure 6:
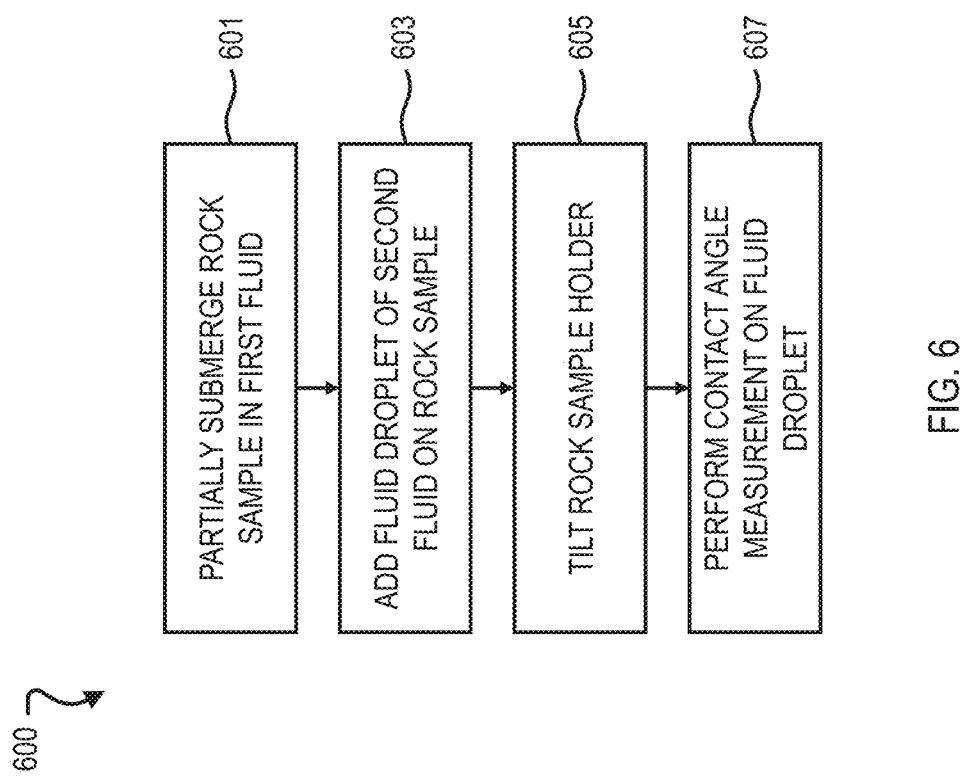
FIG. 6 is a flow chart illustrating an example method for measuring a contact angle.

FIG. 6 is flow chart illustrating an example method 600 for conducting the contact angle measurement test. At 601, a rock sample is at least partially submerged in a first fluid having a first density. The rock sample is supported by a rock sample holder positioned within a housing, for example, the rock sample holder 503 positioned within the housing 500 shown in FIG. 5. In some cases, the first fluid includes water. In some cases, the rock sample is a calcite chip, for example, of Iceland spar.

At 603, a fluid droplet of a second fluid is added on the rock sample. The second fluid has a second density that is lighter than the first density of the first fluid. Due to the difference in densities, the second fluid tends to rise in relation to the first fluid. For example, the first fluid can be water and the second fluid can be a hydrocarbon fluid, such as oil. The fluid droplet of the second fluid can be released from below the rock sample, such that the fluid droplet rises through the first fluid and gets added to the rock sample.

At 605, a rock sample holder is adjusted to be offset from a horizontal while retaining the rock sample on the holder. The rock sample holder is adjusted, such that the rock sample is tilted (that is, an outer surface of the rock sample is at a non-zero angle relative to a lower wall of the housing), thereby causing the fluid droplet to traverse the surface of the rock sample. The rock sample holder can include a stationary plate on a first end of the holder, a moveable plate on a second end of the holder opposite the first end, and a plate-adjusting screw running through a wall of the housing and coupled to the moveable plate. Adjusting the rock sample holder can include adjusting a position of the moveable plate using the plate-adjusting screw. For example, the stationary plate and the moveable plate can be parallel to a horizontal (that is, the stationary plate and the moveable plate can be at the same height with respect to the bottom of the housing) as a base position. The plate-adjusting screw, which is coupled to the moveable plate can be adjusted, so that the moveable plate moves downward (that is, closer to the bottom of the housing). The rock sample, which is seated on the stationary plate and the moveable plate, will tilt based on the offsetting of the moveable plate from the horizontal. At a certain point, the stationary fluid droplet that has been added on the surface of the rock sample will begin to move across (that is, traverse) the surface of the rock sample. Because of the density difference between the first and second fluids, the fluid droplet (which has a lighter density than the second fluid in which the rock sample is at least partially immersed) will roll upward across the rock sample. The plate-adjusting screw can also be adjusted, so that the moveable plate moves upward and return to the base position.

At 607, a contact angle measurement is performed on the fluid droplet with reference to the surface of the rock sample while the fluid droplet traverses the surface of the rock sample. Contact angle measurement can include capturing an image of the fluid droplet on the outer surface of the rock sample and determining a contact angle of the fluid droplet on the outer surface, based on a digitized version of the captured image. For example, a shadow image of the fluid droplet and the rock sample can be obtained using a camera, a light source, an image processing by a computer system to determine contact angle. In some cases, after the contact angle measurement is performed, a sonicator can be used to remove the fluid droplet from the surface of the rock sample while retaining the rock sample on the holder. The sonicator can be used to sonicate the first fluid within the housing to cause the fluid droplet to be removed from the outer surface of the rock sample, and another fluid droplet can be added onto the rock sample to repeat a contact angle measurement. For example, the sonicator can be an ultrasonic transducer positioned in a groove formed on an outer surface of a wall of the housing, and power can be supplied to the ultrasonic transducer in response to which the ultrasonic transducer generates an ultrasonic sound wave that sonicates the fluid droplet.

Figure 7:
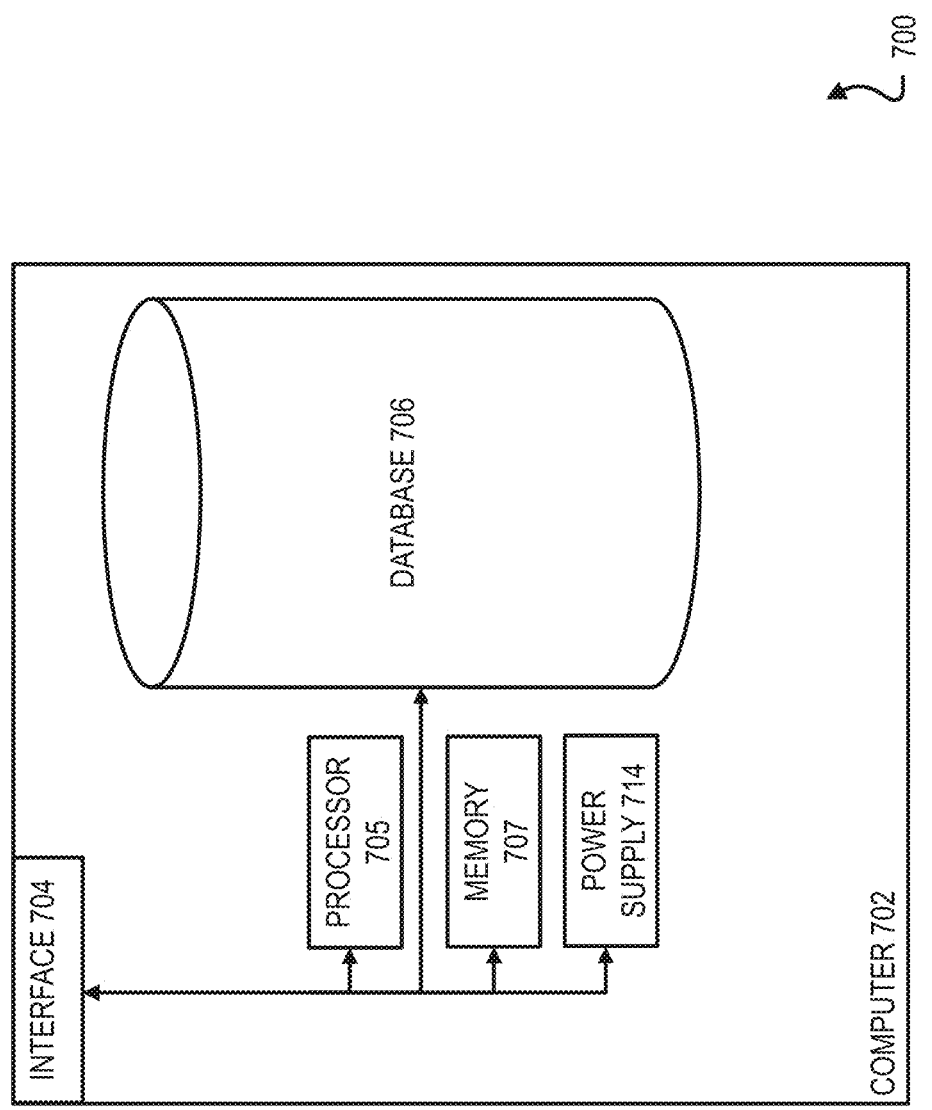
FIG. 7 is a block diagram illustrating an example computer used to provide computational functionalities.

FIG. 7 is a block diagram of an example computer system 700 used to provide computational functionalities associated with described algorithms, methods, functions, processes, flows, and procedures as described in the instant disclosure according to an implementation. The illustrated computer 702 is intended to encompass any computing device such as a server, desktop computer, laptop/notebook computer, one or more processors within these devices, or any other suitable processing device, including physical or virtual instances (or both) of the computing device. Additionally, the computer 702 can include a computer that includes an input device, such as a keypad, keyboard, touch screen, or other device that can accept user information, and an output device that conveys information associated with the operation of the computer 702, including digital data, visual, audio information, or a combination of information.

The computer 702 includes an interface 704. Although illustrated as a single interface 704 in FIG. 7, two or more interfaces 704 may be used according to particular needs, desires, or particular implementations of the computer 702. The interface 704 is used by the computer 702 for communicating with other systems that are connected to the network in a distributed environment. Generally, the interface 704 comprises logic encoded in software or hardware (or a combination of software and hardware) and is operable to communicate with the network. More specifically, the interface 704 may comprise software supporting one or more communication protocols associated with communications such that the network or interface's hardware is operable to communicate physical signals within and outside of the illustrated computer 702.

The computer 702 includes a processor 705. Although illustrated as a single processor 705 in FIG. 7, two or more processors may be used according to particular needs, desires, or particular implementations of the computer 702. Generally, the processor 705 executes instructions and manipulates data to perform the operations of the computer 702 and any algorithms, methods, functions, processes, flows, and procedures as described in the instant disclosure.

The computer 702 can also include a database 706 that can hold data for the computer 702 or other components (or a combination of both) that can be connected to the network. Although illustrated as a single database 706 in FIG. 7, two or more databases (of the same or combination of types) can be used according to particular needs, desires, or particular implementations of the computer 702 and the described functionality. While database 706 is illustrated as an integral component of the computer 702, in alternative implementations, database 706 can be external to the computer 702. The database 706 can include various modelling functions for droplet shapes, such as circular, conic section, polynomial, and Young-Laplace models.

The computer 702 also includes a memory 707 (also referred as computer-readable medium) that can hold data for the computer 702 or other components (or a combination of both) that can be connected to the network. Although illustrated as a single memory 707 in FIG. 7, two or more memories 707 (of the same or combination of types) can be used according to particular needs, desires, or particular implementations of the computer 702 and the described functionality. While memory 707 is illustrated as an integral component of the computer 702, in alternative implementations, memory 707 can be external to the computer 702.

The memory 707 stores computer-readable instructions executable by the processor 705 to perform operations. For example, the operations can include controlling the light source of the image capturing device 191 to shine light at the contact angle measurement apparatus 250 in order to produce a shadow image. The operations can include controlling the camera of the image capturing device 191 to capture the shadow image. The operations can include determining a contact angle between a droplet of fluid and a surface of the rock sample 201 from the shadow image captured by the camera of the image capturing device 191. The operations can include modelling the shape of the droplet of fluid. The operations can include receiving a digitized version of an image of a fluid droplet dropped on a rock sample and determining, based on the image, a contact angle of the fluid droplet relative to a surface of the rock sample on which the fluid droplet is dropped.

In certain implementations, the computer 702 can be connected to the sonicator power source 130, and the computer memory 707 can store computer-readable instructions executable by the processor 705 to perform operations such as controlling the power input supplied to the sonicator 131 in order to vary the amplitude or frequency of sound waves produced by the transducer 135 of the sonicator 131. In certain implementations, the computer 702 can be connected to the heating circuit power source 160, and the computer memory 707 can store computer-readable instructions executable by the processor 705 to perform operations such as controlling the power input supplied to the heater 175 in order to vary the temperature of the heating fluid in the heating circuit 160. The computer 702 can also include a power supply 714. The power supply 714 can include a rechargeable or non-rechargeable battery that can be configured to be either user- or non-user-replaceable.

There may be any number of computers 702 associated with, or external to, a computer system containing computer 702, each computer 702 communicating over the network. Further, the term "client," "user," and other appropriate terminology may be used interchangeably, as appropriate, without departing from the scope of this disclosure. Moreover, this disclosure contemplates that many users may use one computer 702, or that one user may use multiple computers 702.

Thus, particular implementations of the subject matter have been described. Other implementations are within the scope of the following claims.

What is claimed is:

1. A contact angle measurement system comprising:
a housing configured to hold a volume of a first fluid having a first density, the housing comprising:
an upper wall;
a lower wall below the upper wall; and
side walls connecting the upper wall and the lower wall, the upper wall, the lower wall and the side walls defining an enclosure to hold the volume of the first fluid;
an adjustable rock sample holder positioned within the housing, the holder configured to support a rock sample, wherein an orientation of the holder relative to the housing is adjustable such that an outer surface of the rock sample is at a non-zero angle relative to the lower wall of the housing, wherein the holder comprises a stationary plate on a first end of the holder, a moveable plate on a second end of the holder opposite the first end, and a plate-adjusting screw running through the upper wall of the housing and coupled to the moveable plate, the plate-adjusting screw configured to adjust a position of the moveable plate, wherein the upper wall, the lower wall, and the side walls form an enclosure, and the holder is attached to the upper wall;
a fluid dropper attached to the housing, the fluid dropper positioned relative to the holder to add a fluid droplet of a second fluid, whose contact angle is to be measured, on a surface of the rock sample facing the lower wall when the rock sample is supported by the holder, the second fluid having a second density lighter than the first density of the first fluid, wherein, when the orientation of the holder relative to the housing is such that the outer surface of the rock sample is at the non-zero angle relative to the lower wall of the housing, the fluid droplet traverses the outer surface of the rock sample;
an image capturing device configured to capture a plurality of images of the fluid droplet as the fluid droplet traverses the outer surface of the rock sample;
a computer system comprising:
one or more processors, and
a computer-readable medium storing instructions executable by the one or more processors to perform operations comprising:
receiving digitized versions of the plurality of images of the fluid droplet dropped on the rock sample, and
determining, based on one or more of the plurality of images, a contact angle of the fluid droplet relative to a surface of the rock sample on which the fluid droplet is dropped; and
a sonicator attached to the housing, the sonicator configured to generate a sound wave, the housing configured to transmit the sound wave to the fluid droplet on the rock sample, the sound wave configured to sonically remove the fluid droplet from the rock sample.

2. The system of claim 1, further comprising a plurality of clips, each attached to the holder, the plurality of clips spaced apart from each other by a distance in which the holder is positioned.

3. The system of claim 2, further comprising an adjustable screw attached to one of the plurality of clips, the screw configured to change the distance between the plurality of clips.

4. The system of claim 3, wherein the adjustable screw is a first adjustable screw attached to a first of the plurality of clips, the apparatus further comprising a second adjustable screw attached to a second of the plurality of clips, the first adjustable screw and the second adjustable screw independently configured to change the distance between the plurality of clips.

5. The system of claim 1, wherein the first fluid comprises water, and the second fluid comprises hydrocarbon.

6. The system of claim 5, further comprising a heating circuit configured to heat the first fluid, wherein the heating circuit is positioned within the housing.

7. The system of claim 6, wherein the heating circuit is embedded within the lower wall of the housing.

8. The system of claim 7, wherein the heating circuit comprises a fluid-carrying pipe embedded within the lower wall.

9. The system of claim 1, wherein the upper wall of the housing comprises an opening, the fluid dropper comprising a J-needle positioned within the opening in the upper wall of the housing.

10. The system of claim 1, wherein the sonicator comprises a transducer configured to generate the sound wave in response to receiving power from a power source, wherein an outer surface of a wall of the housing comprises a groove, wherein the transducer is embedded in the groove.

11. The system of claim 1, wherein the sonicator is configured to remove the fluid droplet from the rock sample without removing the rock sample or the holder from the housing.

12. A method comprising:
at least partially submerging a rock sample in a first fluid having a first density, the rock sample supported by a rock sample holder positioned within a housing;
adding a fluid droplet of a second fluid on a surface of the rock sample, the second fluid having a second density lighter than the first density of the first fluid;
while retaining the rock sample on the holder, adjusting the rock sample holder to be offset from a horizontal, thereby causing the fluid droplet to traverse the surface of the rock sample;
while the fluid droplet traverses the surface of the rock sample, performing a contact angle measurement on the fluid droplet with reference to the surface of the rock sample; and
after performing the contact angle measurement and while retaining the rock sample on the holder, sonicating the first fluid within the housing to cause the fluid droplet to be removed from the outer surface of the rock sample, wherein the first fluid comprises water, and the medium is sonicated without removing the holder from the housing by:
positioning an ultrasonic transducer in a groove formed on an outer surface of a wall of the housing, and
supplying power to the ultrasonic transducer in response to which the ultrasonic transducer generates an ultrasonic sound wave that sonicates the fluid droplet.

13. The method of claim 12, wherein the holder comprises a stationary plate on a first end of the holder, a moveable plate on a second end of the holder opposite the first end, and a plate-adjusting screw running through a wall of the housing and coupled to the moveable plate.

14. The method of claim 13, wherein adjusting the rock sample holder comprises adjusting a position of the moveable plate using the plate-adjusting screw.

* * * * *